United States Patent [19]

Mims

[11] 4,442,303

[45] Apr. 10, 1984

[54] RECOVERY OF WATER MISCIBLE ORGANIC ACIDS FROM AQUEOUS SOLUTION AS ALKYL ESTERS

[75] Inventor: Samuel S. Mims, Baton Rouge, La.

[73] Assignee: El Paso Products Company, Odessa, Tex.

[21] Appl. No.: 214,790

[22] Filed: Dec. 9, 1980

[51] Int. Cl.³ .................. C07C 67/03; C07C 67/08; C07C 67/54; C07C 67/58; C07C 67/60; C07C 69/003
[52] U.S. Cl. .................. 560/191; 549/231; 549/233; 549/256; 560/129; 560/147; 560/155; 560/174; 560/179; 560/204; 560/217; 560/218; 560/226; 560/234; 560/248; 562/513; 562/530; 562/540; 562/577; 562/580; 562/593; 562/606
[58] Field of Search .............. 560/174, 204, 191, 179, 560/234, 248, 217, 218, 129, 147, 155, 226; 562/530, 593, 513, 538

[56] References Cited

U.S. PATENT DOCUMENTS

| | | | |
|---|---|---|---|
| 3,859,335 | 1/1975 | Schindlbauer et al. | 560/191 |
| 3,896,159 | 7/1975 | Kratzer et al. | 560/191 |
| 4,076,948 | 2/1978 | Mims | 562/593 |
| 4,105,856 | 8/1978 | Newton | 560/191 |

*Primary Examiner*—Vivian Garner
*Attorney, Agent, or Firm*—Depaoli & O'Brien

[57] ABSTRACT

In one of its embodiments this invention provides a process for recovering $C_4$–$C_6$ dicarboxylic acid components contained in a waste byproduct stream derived from a reaction system in which adipic acid is produced by nitric acid oxidation of cyclohexanone/cyclohexanol.

An important aspect of the process is the esterification and extraction of the $C_4$–$C_6$ dicarboxylic acids in the aqueous byproduct stream with a mixture of $C_1$–$C_3$ alkanol and $C_6$–$C_{20}$ alkanol, and the subsequent recovery of di($C_6$–$C_{20}$ alkyl) esters of succinic acid, glutaric acid and adipic acid.

18 Claims, 1 Drawing Figure

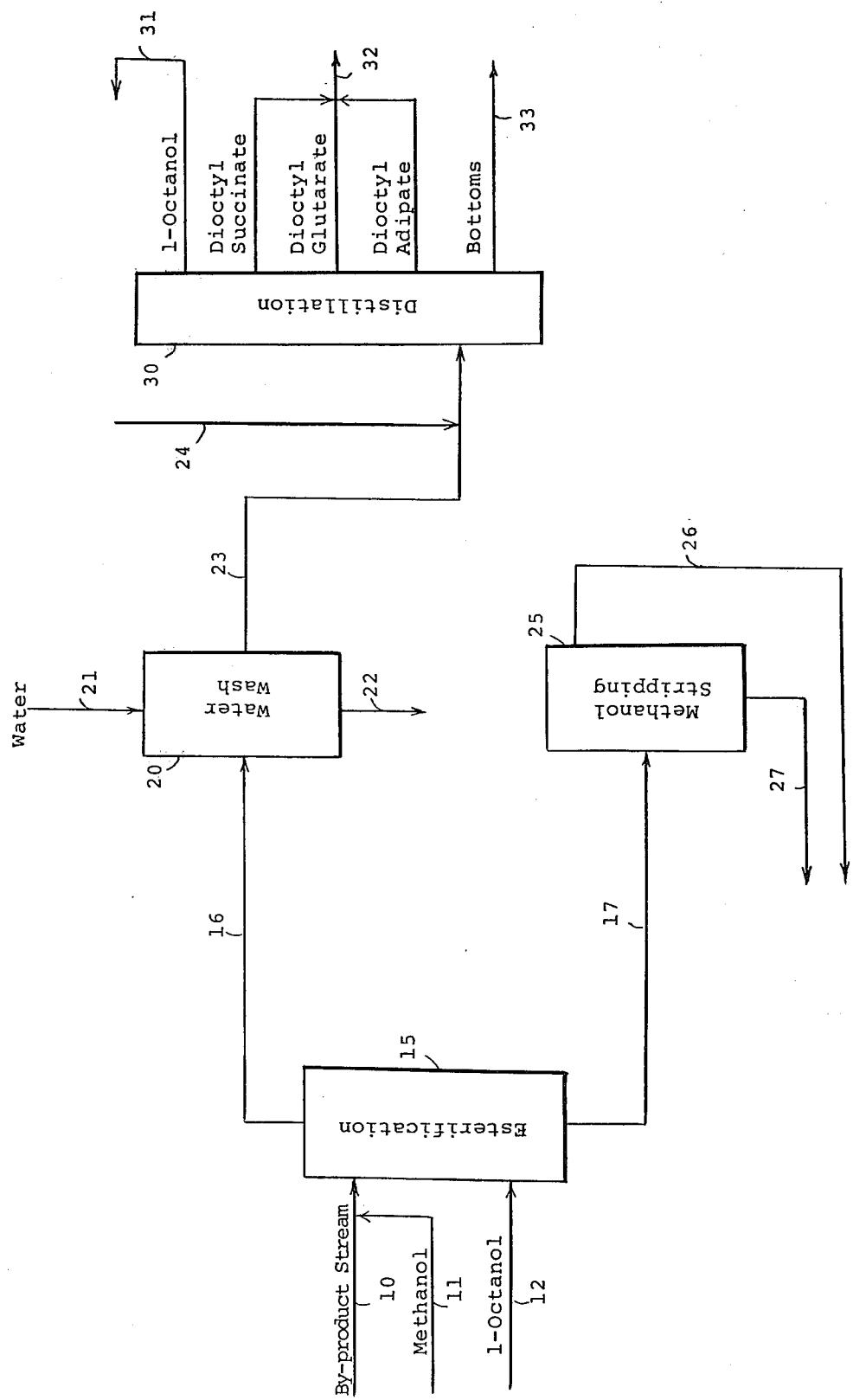

RECOVERY OF WATER MISCIBLE ORGANIC ACIDS FROM AQUEOUS SOLUTION AS ALKYL ESTERS

BACKGROUND OF THE INVENTION

Commercial methods for producing dicarboxylic acids generally involve oxidizing naphthenes, cycloaliphatic ketones or cycloaliphatic alcohols with nitric acid in the presence of metal oxidation catalysts.

In the case of adipic acid, specific feed materials such as cyclohexane, cyclohexanol and/or cyclohexanone in admixture with nitric acid are heated at about 40°–140° C. in the presence of a catalyst. The resultant oxidation reaction product comprises adipic acid together with small amounts of monocarboxylic acids and dicarboxylic acids and other organic components in admixture with nitric acid and catalyst components. A substantial quantity of the adipic acid product is recovered by cooling the solution and filtering off the crystallized adipic acid. Oxidation methods of adipic acid production are described in U.S. Pat. Nos. 2,439,513; 2,557,281; 2,719,566; 2,840,607; 2,971,010; 3,338,959; and references cited therein.

In a process involving nitric acid oxidation of cyclohexanone and/or cyclohexanol, economically significant amounts of succinic acid and glutaric acid are formed as byproducts in admixture with adipic acid. After the major portion of the adipic acid is separated by crystallization and filtration, the filtrate mother liquor contains some adipic acid, as well as succinic acid, glutaric acid, nitric acid and metal catalyst values.

Usually this filtrate has been treated as a waste stream. Because of environmental and economic considerations, there has been continuing research effort to develop methods for recovering the valuable and reusable organic and inorganic components of the said filtrate waste byproduct stream.

U.S. Pat. No. 3,726,888 describes a process for the separation and recovery of the components contained in the filtrate waste byproduct stream of an adipic acid manufacturing plant. The filtrate stream comprises a mixture of adipic acid, glutaric acid, succinic acid, nitric acid and metal catalyst values. The separation and recovery process involves contacting the filtrate with alkanol, and extracting with a water-immiscible organic solvent to provide an organic phase containing the formed esters, and to provide an aqueous phase containing the nitric acid and metal catalyst values. Each of the phases is fractionated to separate the mixtures into useful components.

U.S. Pat. Nos. 4,058,555; 4,076,948 and 4,082,788 describe processing improvements which are adapted to overcome some of the difficulties characteristic of the byproduct separation and recovery technology disclosed in the above recited U S. Pat. No. 3,726,888.

U.S. Pat. No. 3,786,096 describes a carboxylic acid recovery process which involves subjecting a mixture of adipic acid and succinic acid to an extraction process wherein an extractant system of water and cyclohexanone and/or cyclohexanol is employed to achieve preferential extraction of adipic acid into an organic phase.

U.S. Pat. No. 3,790,626 describes a method of purifying adipic acid prepared by oxidizing cyclohexane/cyclohexanone/cyclohexanol which method involves subjecting the raw adipic acid crystals to nitric acid treatment, and recrystallizing the treated adipic acid from water.

In U.S. Pat. No. 3,983,208, an aqueous nitric acid solution derived from an adipic acid process containing copper and vanadium catalyst values and dicarboxylic acids is treated to remove the nitric acid and water and yield a substantially dry solid residue. The said solid residue is mixed with a dialkyl ketone solvent which dissolves the dicarboxylic acids and leaves the catalyst metal values as solids.

U.S. Pat. No. 3,991,100 describes a three-step process for making alkyl esters of dicarboxylic acids contained in an adipic acid plant waste stream, which involves distilling the stream to remove water and nitric acid, esterifying the dicarboxylic acids in the residual concentrate, and distilling the esterification product mixture in the presence of a dry base such as sodium carbonate.

U.S. Pat. No. 4,014,903 describes a method of recovering dicarboxylic acids from an adipic acid plant waste stream which involves stripping nitric acid from the waste stream with steam, and thereafter subjecting the nitric acid-free stream to distillation to recover useful products.

U.S. Pat. No. 4,105,856 describes a method for recovering organic and inorganic values from an adipic acid plant waste stream which involves contacting the waste stream with a $C_4$–$C_{20}$ alcohol to form a water-immiscible ester phase, separating the said ester phase from the aqueous phase, and recycling the aqueous phase to the adipic acid oxidation unit.

Also in connection with treatment of an adipic acid plant waste stream, U.S. Pat. No. 4,146,730 describes a process which comprises the steps of contacting the waste stream with urea to separate out and recover a urea-glutaric acid adduct, contacting the waste stream again to separate out and recover a urea-succinic acid adduct, and thereafter decomposing the adducts to yield the respective dicarboxylic acids.

As indicated by the prior art references described above, investigative effort to recover values from manufacturing plant waste streams is a high priority commitment.

Accordingly, it is an object of this invention to provide an improved process for the recovery of organic acids from dilute aqueous solutions.

It is another object of this invention to provide an improved process for the separation and recovery of dicarboxylic acids and other valuable components contained in a filtrate byproduct stream derived from an adipic acid manufacturing operation involving nitric acid oxidation of cyclohexanol and/or cyclohexanone.

It is another object of this invention to recover catalyst values contained in a filtrate byproduct stream derived from an adipic acid manufacturing operation involving nitric acid oxidation of cyclohexanone and/or cyclohexanol, wherein the recovered catalyst values are contained in an aqueous phase suitable for recycle.

It is a further object of this invention to recover $C_4$–$C_6$ byproducts from an adipic acid manufacturing operation involving nitric acid oxidation of cyclohexanone and/or cyclohexanol, wherein the recovered $C_4$–$C_6$ byproducts are in the form of dicarboxylic acid diesters.

Other objects and advantages of the present invention shall become apparent from the accompanying description and Examples

DESCRIPTION OF THE INVENTION

As noted previously, in the oxidation of cyclohexanone and/or cyclohexanol with nitric acid in the presence of a metal oxidation catalyst, the resulting oxidation product solution is processed for recovery of the bulk of the desired adipic acid by crystallization and filtration. The adipic acid mother liquor (i.e., the aqueous filtrate byproduct stream) contains quantities of monobasic and dibasic carboxylic acids as well as nitric acid and metal catalyst values. These filtrate components are sufficiently valuable to invite the application of recovery procedures, particularly in view of the environmental protection ramifications.

A typical filtrate byproduct stream nominally corresponds to the following weight percent composition:

| Component | Amount |
|---|---|
| Succinic acid | 3-10% |
| Glutaric acid | 8-35% |
| Adipic acid | 3-6% |
| Nitric acid | 6-20% |
| Catalyst | 1-3% |
| Water | Balance |

The catalyst values contained in the filtrate are those which are conventionally employed in cyclohexanone/cyclohexanol oxidation procedures, such as copper, vanadium, and the like.

The present invention process is adapted to improve the material balance associated with the separation and recovery of $C_4$-$C_6$ dicarboxylic acid components which are contained in the said filtrate byproduct stream of an adipic acid manufacturing operation, and the material balance associated with the separation and recovery of metal catalyst values in a form suitable for recycle to the cyclohexanone/cyclohexanol oxidation system.

Thus, one or more objects of the present invention are accomplished by the provision of a process for recovery of $C_4$-$C_6$ dicarboxylic acid components contained in an aqueous filtrate, which filtrate is a waste byproduct stream derived from a reaction system in which adipic acid is produced by nitric acid oxidation of cyclohexanone/cyclohexanol, wherein the process comprises the steps of (1) contacting the said aqueous stream with a mixture of $C_1$-$C_3$ alkanol and $C_6$-$C_{20}$ alkanol to esterify the $C_4$-$C_6$ dicarboxylic acid components; (2) separating the formed water-immiscible organic ester phase from the aqueous phase; and (3) distilling the said organic ester phase to yield di($C_6$-$C_{20}$ alkyl) esters of succinic acid, glutaric acid and adipic acid.

In a further embodiment, this invention provides a process for recovery of $C_4$-$C_6$ dicarboxylic acid components contained in an aqueous filtrate, which filtrate is a waste byproduct stream derived from a reaction system in which adipic acid is produced by nitric acid oxidation of cyclohexanone/cyclohexanol, wherein the process comprises the steps of (1) contacting the said aqueous stream with a mixture of $C_1$-$C_3$ alkanol and $C_6$-$C_{20}$ alkanol at a temperature between about 40°-100° C. to esterify the $C_4$-$C_6$ dicarboxylic acid components, where at least about two moles of each of the $C_1$-$C_3$ alkanol and $C_6$-$C_{20}$ alkanol reactants are present per mole of $C_4$-$C_6$ dicarboxylic acids; (2) separating the formed water-immiscible organic ester phase from the aqueous phase; (3) distilling the said organic ester phase to yield di($C_6$-$C_{20}$ alkyl) esters of succinic acid, glutaric acid and adipic acid; (4) concentrating the said aqueous phase from step(2) by distillation to provide an aqueous concentrate solution containing nitric acid and metal catalyst values.

The step(1) esterification of the $C_{4-6}$ dicarboxylic acids can be conducted at any temperature between about room temperature and the boiling point of the esterification reaction medium. A suitable temperature is one in the range between about 40°-100° C., and preferably the temperature is maintained in the range between about 45°-75° C. The esterification reaction time on the average will vary in the range between about 0.5-2 hours, depending on the temperature, choice of alkanols, and other controlling processing parameters.

An important aspect of the invention process is the use of a combination of $C_{1-3}$ alkanol and $C_6$-$C_{20}$ alkanol as esterification reactants. Illustrative of $C_{1-3}$ alkanols are methanol, ethanol, propanol and isopropanol. Illustrative of $C_{6-20}$ alkanols are hexanol, 2-hexanol, 2,3,3-trimethyl-2-butanol, 2-methyl-2-hexanol, 2-ethylhexanol, octanol, decanol, dodecanol, eicosanol, and the like. The alkanols employed can contain non-interfering heteroatoms such as nitrogen and sulfur, and substituents such as halogen, and aromatic and alicyclic groups.

Effectively, the $C_{1-3}$ alkanol is selected to function as a water-miscible reactant, and the $C_{6-20}$ alkanol is selected to function as a water-immiscible reactant. Hence, during the esterification step of the process the following reaction mechanism occurs in the aqueous phase:

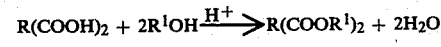

At the same time, a partial transesterification reaction mechanism occurs in the water-immiscible organic phase:

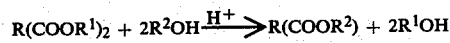

In the above equations, R is a $C_{2-4}$ alkylene group, $R^1$ is a $C_{1-3}$ alkyl group, $R^2$ is a $C_{6-20}$ alkyl group, and $H^+$ is an acidic pH provided by the nitric acid component present in the esterification medium.

It is preferred that at least two moles of $C_{1-3}$ alkanol and two moles of $C_{6-20}$ alkanol are employed for each mole of $C_{4-6}$ dicarboxylic acids being esterified. Normally an excess of each alkanol is employed to compensate for other carboxylic acids such as oxalic acid, butyric acid, valeric acid and caproic acid which may be present in small quantities. Also, an excess of alkanol causes a favorable reaction equilibrium shift toward the desired ester formation.

During the esterification reaction period, it is advantageous to employ efficient stirring in order to provide intimate admixing and contacting between the aqueous phase and the water-immiscible organic phase. This facilitates the transfer of the initially formed $C_{1-3}$ alkanol diester from the aqueous phase into the water-immiscible organic phase, in which phase the said $C_{1-3}$ alkanol diester undergoes at least partial transesterification (i.e., alcoholysis) with the $C_{6-20}$ alkanol reactant.

After the esterification step(1) is completed, the two immiscible phases are allowed to separate (e.g., in a separation tank). The esterification step(1) and the phase separation step(2) preferably are conducted on a continuous basis.

The phase separation procedure will require between about 0.1–1.0 hour, depending to some degee on the temperature of the phase volumes. A preferred temperature for the separation procedure is one in the range between about 10°–40° C.

After the aqueous phase and water-immiscible organic ester phase are separated and recovered, each is subjected to further manipulative procedures.

The organic ester phase may be charged directly to a distillation unit without an intervening water-wash step. Without a water-wash treatment, there is present an entrained quantity of nitric acid in the organic ester phase which subsequently functions as a transesterification catalyst in the distillation phase of the process.

As noted in the drawing, alternatively the organic ester phase can be water-washed to remove the entrained nitric acid, and then a selected transesterification catalyst is incorporated in the organic ester phase prior to or during the distillation operation. Particularly efficient transesterification catalysts include metal alkoxides such as sodium alkoxide, potassium ethoxide, titanium butoxide, and the like. Non-oxidizing mineral acids such as phosphoric acid are also suitable transesterification catalysts.

Distillation step(3) of the process accomplishes at least two important objectives.

First, during the early stages of the distillation the lower boiling $C_{1-3}$ alkanol is removed as an overhead fraction. This shifts the alcoholysis equilibrium until substantially all of the $C_{1-3}$ alkanol diester is converted to $C_{6-20}$ alkanol diester.

Second, the $C_{6-20}$ alkanol diester product is recovered either as a mixed diester fraction, or as individually pure components. The said diester product yield comprises di($C_{6-20}$ alkyl) esters of succinic acid, glutaric acid and adipic acid. Recovering the alkanol diesters or individually pure components requires specialized distillation equipment. The economics of the process favors recovery of a mixed diester fraction.

In the form of a high molecular weight mixed diester fraction, the invention product is valuable per se for use as a plasticizer for resins such as polyvinyl chloride.

In most cases, the said distillation of the organic ester phase yields a small quantity of $C_{6-20}$ alkanol monoesters of succinic acid, glutaric acid and adipic acid. These monoesters can be recycled to esterification step(1) of the process.

With respect to the further processing of the recovered aqueous phase, preferably it is concentrated by distillation in vacuo to provide an aqueous concentrate solution. The distillation removes some of the water, as well as residual $C_{1-3}$ alkanol and other volatile organic components which co-distill with water. As desired, the distillation conditions can be controlled to cause either a small portion or a large portion of the nitric acid content of the aqueous phase to distill overhead.

The aqueous concentrate solution which results from the distillation contains nitric acid and metal catalyst values. Usually the catalyst values will comprise compounds of metals such as vanadium and copper.

It is an important aspect of the invention process that the aqueous concentrate solution described above has excellent properties which qualify its use for recycle to the cyclohexanone/cyclohexanol oxidation stage of the primary adipic acid production system.

The practice of the present invention as a continuous process can be better understood by reference to the drawing which is illustrated as a flow diagram.

In the drawing, a byproduct stream from an adipic acid plant is fed through line 10 into Esterification unit 15. At the same time, methanol is fed through line 11 and 1-octanol is fed through line 12 into Esterification unit 15. The esterification reaction is conducted at a temperature of 60° C. during a residence period of about 20 minutes to form methyl esters of $C_4$–$C_6$ dicarboxylic acids.

The aqueous solution of esterified byproduct stream and excess methanol descend in countercurrent contact with the ascending 1-octanol stream. The water-immiscible organic phase of 1-octanol and extracted esters is withdrawn continuously from Esterification unit 15 through line 16 and introduced into Water Wash unit 20, and there it is contacted countercurrently with water which is fed through line 21 into Water Wash unit 20.

The aqueous phase passing downward through Esterification unit 15 is transferred via line 17 into Methanol Stripping unit 25. The stripped methanol is recycled to Esterification unit 15 through line 26, and the residual aqueous concentrate solution containing nitric acid and vanadium and copper catalyst values is recycled from Methanol Stripping unit 25 to the primary adipic acid production system through line 27.

The spent water wash stream from Water Wash unit 20 is withdrawn through line 22 and removed from the system for subsequent salvage processing. The washed organic stream is recovered from Water Wash unit 20 through line 23 and fed into Distillation unit 30. A methanolic solution of sodium methoxide catalyst passed through line 24 and admixed with the organic stream in line 23 before it enters Distillation unit 30.

1-Octanol is recycled through line 31 to Esterification unit 15. Lines 32 and 33 are employed to isolate the dioctyl succinate/dioctyl glutarate/dioctyl adipate and bottoms fractions, respectively.

As it is apparent from the foregoing description, the present invention process is particularly advantageous for the recovery of $C_4$–$C_6$ carboxylic acids which are contained in the byproduct stream from an adipic acid manufacturing plant. The said process is sufficiently versatile to be applied in general to the recovery of organic acids from dilute aqueous solutions.

Hence, in a broader aspect this invention provides a process for recovery of water-miscible organic acid components contained in an aqueous solution which comprises the steps of (1) contacting the said aqueous stream with a mixture of $C_1$–$C_3$ alkanol and $C_6$–$C_{20}$ alkanol under acidic conditions to esterify the organic acid components; (2) separating the formed water-immiscible organic ester phase from the aqueous phase; and (3) distilling the said organic ester phase to recover $C_6$–$C_{20}$ alkyl esters of the organic acids. The distillation preferably is conducted in the presence of a transesterification catalyst, e.g, in a quantity between about 0.05–2 percent based on the weight of mixed esters.

As noted previously, the transesterification reaction can be catalyzed by the presence of a strong mineral acid such as sulfuric acid., hydrochloric acid, or phosphoric acid, or a basic type catalyst such as a metal alkoxide. Also suitable is a solid type of catalyst, such as an ion exchange resin in the free acid form. The solid type of acid catalyst has the advantage that it can be easily separated from the medium.

The following examples are further illustrative of the present invention. The reactants and other specific ingredients are presented as being typical, and various modifications can be derived in view of the foregoing disclosure within the scope of the invention.

EXAMPLE I

An aqueous solution is prepared containing 5 percent succinic acid, 5 percent adipic acid and 10 percent nitric acid.

One volume of the prepared solution is admixed with one volume of methanol and one volume of 1-octanol.

The admixture is stirred at 50° C. for one hour, and then it is allowed to stand at room temperature until there is clear separation between the aqueous and water-immiscible organic phases.

Gas chromatographic analysis of the organic phase indicates that it contains major quantities of dimethyl succinate, dimethyl adipate, methyl octyl succinate and methyl octyl adipate, and minor quantities of dioctyl succinate and dioctyl adipate.

The organic phase is subjected to distillation, and methanol and 1-octanol are removed as distillate. Analysis of the organic concentrate indicates that it is substantially dioctyl succinate and dioctyl adipate, without any evidence of any methyl esters.

EXAMPLE II

A 1.4 inch diameter glass extractor apparatus is packed with ⅜ inch ceramic intalox saddles. It is water-jacketed, and has a hold up volume of about 600 milliliter.

A mixture with the following composition is prepared:

| | |
|---|---|
| Adipic Acid | 10.7% |
| Glutaric Acid | 13.4 |
| Succinic Acid | 10.7 |
| Nitric Acid | 9.3 |
| Water | 55.9 |
| | 100.0% |

This mixture is similar in composition to the waste stream from an adipic acid manufacturing plant except that it does not contain copper and vanadium catalysts. Methanol is added to the mixture to yield the extractor feed:

| | |
|---|---|
| Adipic Acid | 7.7% |
| Glutaric Acid | 9.7 |
| Succinic Acid | 7.7 |
| Nitric Acid | 6.8 |
| Water | 40.4 |
| Methanol | 27.7 |
| | 100.0% |

The feed is added to the top of the described extractor at the rate of 16 milliliters/minute, and an equal volume of 1-octanol is entered into the bottom. The extractor is operated in a countercurrent fashion with the aqueous phase as the continuous phase. The temperature of the water jacket is adjusted to maintain a temperature of 60° C. in the liquid at the top of the extractor. The extract phase exits from a side outlet.

The extractor is operated continuously and is monitored by examining the extract and raffinate by gas chromatography. These analyses indicate that greater than 95% of each of the organic acids had been removed from the feed and are present in the extract predominantly as the dimethyl esters The 1-octanol extract is recovered and charged to a distillation unit, and methanol, water and octanol are distilled out of the mixture over a three hour period employing an efficient distillation column. Examination of the extract remaining in the still indicates high conversion of the esters to dioctyl succinate, glutarate and adipate. A small (~3%) quantity of mixed methyl octyl esters is also present.

A comparison run employing benzene as the extractant-reactant demonstrates that 1-octanol is more efficient for removal of the organic acids. Benzene removes about 85% of these acids versus the greater than 95% noted above for the 1-octanol extractant-reactant.

When 1-butanol is employed as the prospective extractant-reactant, the countercurrent system is inoperable since there is no formation of immiscible organic and aqueous phases.

The process operates satisfactorily when 1-hexanol is the extractant-reactant, except that less methanol and a lower temperature must be employed in comparison to the system employing 1-octanol as the extractant-reactant.

EXAMPLE III

Employing the same extractor system described in Example II, the invention process is conducted with 1-decanol as the extractant-reactant, and the didecyl ester products are recovered by distillation.

The weight balance in the extractor system is as follows:

| | IN | | OUT |
|---|---|---|---|
| Feed | 2667 g | Raffinate | 2043 g |
| Extractant | 1929 g | Extract | 2497 g |
| | 4596 g | | 4540 g |

The extraction efficiency of 1-decanol is slightly less than that of 1-octanol. The extraction efficiency of 2-ethylhexanol is approximately the same as 1-octanol.

EXAMPLE IV

A feed solution is prepared which had the following composition:

| | |
|---|---|
| Succinic Acid | 7.1% |
| Glutaric Acid | 8.7 |
| Adipic Acid | 7.1 |
| Sulfuric Acid | 1.3 |
| Water | 50.5 |
| Methanol | 25.3 |
| | 100.0% |

The mixture is extracted with 1-octanol employing the same extraction system as described in Example II. The weight balance in the system is as follows:

| | IN | | OUT |
|---|---|---|---|
| Feed | 1816 g | Raffinate | 1249 g |
| Extractact | 1476 g | Extract | 2043 g |
| | 3292 g | | 3292 g |

The extract contains mostly dimethyl esters of the dibasic acids. On removal of methanol and water by distillation, the dimethyl esters are converted to dioctyl esters.

EXAMPLE V

Technical grade lactic acid as a 44% aqueous solution (500 grams) is mixed with ethanol (500 grams) and sulfuric acid (96%, 50 grams).

At a temperature of about 50° C., the lactic acid feed is passed downward in countercurrent contact with 1-octanol in an extractor system similar to that described in Example II.

White-white octyl lactate of greater than 90% purity is obtained in about 50% yield.

Technical grade levulinic acid can be converted to octyl levulinate employing the same extractor system described above. Vacuum distillation of the recovered product yields an octyl levulinate fraction of about 99% purity.

EXAMPLE VI

A filtrate byproduct stream from an adipic acid plant contains 18.4 weight percent nitric acid, 19.3 weight percent dibasic organic acids calculated as adipic acid, and catalyst values of vanadium and copper.

About 100 grams of the filtrate is admixed with 40 grams of ethanol and 40 grams of 1-hexanol. The admixture is stirred at 60° C. for 20 minutes, and then cooled to room temperature to allow separation of the aqueous and organic phases.

Analysis of the aqueous phase indicates that it contains 17 weight percent nitric acid, and 0.6 weight percent organic acids calculated as adipic acid.

The aqueous phase is separated from the organic phase and concentrated by vacuum distillation to yield an aqueous concentrate solution containing nitric acid and vanadium and copper catalyst values.

The organic phase is washed with water several times, then it is charged to a fractional distillation unit. Ethanol and 1-hexanol are removed overhead, and dihexyl succinate, dihexyl glutarate and dihexyl adipate are recovered as separate distillate fractions.

For purposes of the present invention, the fractional distillation system can comprise a single distillation column or a series of distillation columns. For example, the organic phase described above first is passed through a stripping unit to remove ethanol and 1-hexanol and other light ends. Then the organic phase recovered from the stripping unit is fed into a first distillation unit which is controlled to distill the lowest boiling ester components, e.g., dihexyl oxalate. Simultaneously, dihexyl succinate is withdrawn from the side of the column. The residual higher boiling ester fraction is recovered and passed into a second distillation unit, wherein dihexyl glutarate is distilled overhead and dihexyl adipate is separated as a side draw, leaving a distillation bottoms residuum Nominally the residual bottoms fraction contains succinic acid, glutaric acid, adipic acid, and monohexyl esters thereof, in addition to other components such as succinic and glutaric anhydrides and relatively nonvolatile tars and resins.

What is claimed is:

1. A process for recovery of $C_4$–$C_6$ dicarboxylic acid components contained in an aqueous waste byproduct stream resulting from a primary reaction system in which adipic acid is produced by nitric acid oxidation of cyclohexanone/cyclohexanol, wherein the process comprises the steps of (1) contacting the said aqueous stream with a mixture of $C_1$–$C_3$ alkanol and $C_6$–$C_{20}$ alkanol to esterify the $C_4$–$C_6$ dicarboxylic acid components; (2) separating the formed water-immiscible organic ester phase from the aqueous phase; and (3) distilling the said organic ester phase to yield di($C_6$–$C_{20}$ alkyl) esters of succinic acid, glutaric acid and adipic acid.

2. A process in accordance with claim 1 wherein the separate aqueous phase recovered in step(2) is concentrated by distillation to provide an aqueous concentrate solution containing nitric acid and metal catalyst values.

3. A process in accordance with claim 1 wherein the di($C_6$–$C_{20}$ alkyl) esters in step(3) are recovered as a mixed ester fraction.

4. A process in accordance with claim 1 wherein the di($C_6$–$C_{20}$ alkyl) esters are recovered as individual components.

5. A process in accordance with claim 1 wherein monoesters of $C_4$–$C_6$ dicarboxylic acids additionally are recovered in step(3) and recycled to step(1) of the process.

6. A process for recovery of $C_4$–$C_6$ dicarboxylic acid components contained in an aqueous waste byproduct stream resulting from a primary reaction system in which adipic acid is produced by nitric acid oxidation of cyclohexanone/cyclohexanol, wherein the process comprises the steps of (1) contacting the said aqueous stream with a mixture of $C_1$–$C_3$ alkanol and $C_6$–$C_{20}$ alkanol at a temperature between about 40°–100° C. To esterify the $C_4$–$C_6$ dicarboxylic acid components, where at least about two moles of each of the $C_{1-3}$ alkanol and $C_{6-20}$ alkanol reactants are present per mole of $C_4$–$C_6$ dicarboxylic acids; (2) separating the formed water-immiscible organic ester phase from the aqueous phase; (3) distilling the said organic ester phase to yield di($C_6$–$C_{20}$ alkyl) esters of succinic acid, glutaric acid and adipic acid; and (4) concentrating the said aqueous phase from step(2) by distillation to provide an aqueous concentrate solution containing nitric acid and metal catalyst values.

7. A process in accordance with claim 6 wherein the $C_{1-3}$ alkanol is methanol.

8. A process in accordance with claim 6 wherein the $C_{6-20}$ alkanol is hexanol.

9. A process in accordance with claim 6 wherein the $C_{6-20}$ alkanol is 2-ethylhexanol.

10. A process in accordance with claim 6 wherein the $C_{6-20}$ alkanol is octanol.

11. A process in accordance with claim 6 wherein the $C_{6-20}$ alkanol is decanol.

12. A process in accordance with claim 6 wherein the di($C_6$–$C_{20}$ alkyl) esters in step(3) are recovered as a mixed ester fraction.

13. A process in accordance with claim 6 wherein the metal catalyst values in the step(4) aqueous concentrate solution comprise vanadium and copper.

14. A process for recovery of water-miscible organic acid components contained in an aqueous solution which comprises the steps of (1) contacting the said aqueous stream with a mixture of $C_1$–$C_3$ alkanol and $C_6$–$C_{20}$ alkanol under acidic conditions to esterify the organic acid components; (2) separating the formed water-immiscible organic ester phase from the aqueous phase; and (3) distilling the said organic ester phase to recover $C_6$–$C_{20}$ alkyl esters of the organic acids.

15. A process in accordance with claim 14 wherein the acidic conditions in step(1) are provided by the presence of a mineral acid.

16. A process in accordance with claim 14 wherein the step(3) distillation is conducted in the presence of an added transesterification catalyst.

17. A process in accordance with claim 16 wherein the transesterification catalyst is a non-oxidizing mineral acid.

18. A process in accordance with claim 16 wherein the transesterification catalyst is a metal alkoxide.

* * * * *